United States Patent [19]

Behrmann et al.

[11] Patent Number: 5,382,748
[45] Date of Patent: Jan. 17, 1995

[54] HYDROCARBON SYNTHESIS REACTOR EMPLOYING VERTICAL DOWNCOMER WITH GAS DISENGAGING MEANS

[75] Inventors: William C. Behrmann; Charles H. Mauldin; Larry E. Pedrick, all of Baton Rouge, La.

[73] Assignee: Exxon Research & Engineering Co., Florham Park, N.J.

[21] Appl. No.: 994,218

[22] Filed: Dec. 18, 1992

[51] Int. Cl.[6] .................. C07C 7/20; B01J 20/34; B01J 9/08
[52] U.S. Cl. .................... 585/899; 585/922; 585/924; 502/34; 422/219
[58] Field of Search ............. 585/899, 922, 924; 502/34; 422/219

[56] References Cited

U.S. PATENT DOCUMENTS

| | | | |
|---|---|---|---|
| 2,287,092 | 6/1942 | Duftschmid et al. | 260/449 |
| 2,853,369 | 9/1958 | Kolbel et al. | 23/288 |
| 2,868,627 | 1/1959 | Kolbel et al. | 23/288 |
| 3,414,386 | 12/1968 | Mattix | 23/288 |
| 3,629,143 | 12/1971 | Reveal | 252/411 |
| 4,751,057 | 6/1988 | Westerman | 422/197 |
| 5,157,054 | 10/1992 | Herbolzheimer et al. | 518/700 |
| 5,211,917 | 5/1993 | Hookham | 422/139 |
| 5,219,532 | 6/1993 | Buttke et al. | 422/140 |

OTHER PUBLICATIONS

"Effects of Fine Bubbles on Flow Patterns in Bubble Column with Suspended Solid Particles" Morooka, et al, J. Chem Eng. of Japan, vol. 19, No. 6, 1986, pp. 507–512.
"Gas Holdup and Volumetric Liquid-Phase Mass Transfer Coefficient in Solid Suspended Bubble Column with Draught Tube", Koide, et al, J. Chem Eng. of Japan, vol. 18, No. 3, 1985, pp. 248–254.
"Application of Airlift Gas-Liquid-Solid Reactors in Biotechnology", Siegel and Robinson, Chem Eng. Science vol. 47, No. 13/14, pp. 3215–3229, 1992.
"The Catalytic Synthesis of Hydrocarbons from $H_2/CO$ Mixtures over the Group VIII Metals", Vannice, J of Catalysis 37, 449–461, (1975).
"Hydrocarbon Synthesis, Hydrogenation and Cyclization" Emmett, Catalysis, vol. IV, pp. 103–108, Reinhold Publishing Corp. 1956.
"Titania-Supported Metals as CO Hydrogenation Catalysts", Vannice, Journal of Catalysis 74, 199–202 (1982).
"Sparged Loop Reactors" Joshi et al, The Canadian Journal of Chemical Engineering, vol. 68, Oct. 1990, 705–741.
"Reaction Technology in Bubble Colums" Deckwer, Fundamentals of Chemical Technology Process Technology of the Chemical and Related Industries, Otto Salle Verlag Publishers, Sauerlander Publishing 1985, Chapter 1.
"Loop Reactors" Blenke, Adv. Biochem Eng. vol. 13, 1979, pp. 121–214.

*Primary Examiner*—Asok Pal
*Assistant Examiner*—Nhat D. Phan
*Attorney, Agent, or Firm*—Joseph J. Allocca

[57] ABSTRACT

The operation of a hydrocarbon synthesis reactor and catalyst distributed in the reaction slurry therein are improved by the presence in said reactor of one or more vertical downcomers open at both ends with gas disengaging areas located at their top end. The downcomer which circulates catalyst from the top of the reaction slurry to the bottom of said slurry is fully immersed in the reaction slurry and preferably extends from just above the bottom of the reaction zone of the reaction vessel to just below the top surface of the reaction slurry. The bottom end of said downcomer is shielded from intrusion of rising synthesis gas by the placement of a baffle which blocks rising gas entry but facilitates the exit of catalyst and liquid from the bottom of said downcomer and distributes them radially throughout the adjacent reactor slurry.

6 Claims, 4 Drawing Sheets

HYDROCARBON SYNTHESIS REACTOR EMPLOYING VERTICAL DOWNCOMER WITH GAS DISENGAGING MEANS

FIELD OF THE INVENTION

The present invention relates to a method and a means for improving the operation of a hydrocarbon synthesis process and the distribution of catalyst in a reactive slurry comprising catalyst in hydrocarbon synthesis product and synthesis process feed gases in slurry phase reactors used in said process. Catalyst circulation is improved and catalyst distribution in said reaction slurry is made more uniform by the presence of substantially vertical conduit means in the reaction zone of the hydrocarbon synthesis process. The downcomer is a substantially vertical conduit means, open at both ends, is fully submerged in the reaction slurry, the bottom end of which substantially vertical conduit means is near the bottom of the reaction zone of the reaction process and the top end of which is topped by gas disengaging means and is below the top surface of the reaction slurry in the reaction zone of the reaction process. For simplicity the substantially vertical conduit means will hereafter be referred to as a downcomer or downcomers. The downcomer circulates the catalyst and liquid slurry from the top of the slurry back down to the bottom of the slurry, helping to prevent stagnant zones by stimulating such catalyst and liquid circulation in the reaction slurry. Such movement also promotes more uniform catalyst utilization and more uniform catalyst aging in the process while reducing the back mixing of the synthesis process feed gases. It also promotes a more uniform temperature within the reaction zone with consequent better utilization of heat transfer area.

BACKGROUND OF THE INVENTION

Slurry reactors are well known for carrying out highly exothermic, three phase, catalytic reactions. Usually called "bubble columns" these reactors have a liquid phase in which solid catalyst particles are dispersed or held in suspension by a gas phase bubbling through the liquid phase, thereby creating a slurry. These reactors provide improved heat transfer characteristics for the exothermic reaction, and the bubbling gas maintaining the catalyst dispersed in the liquid phase.

Bubble column reactors typically have a multiplicity of tubes suspended within a shell-type housing, the tubes being filled with a heat transfer medium, e.g., boiling water, which absorbs the heat generated by the exothermic reaction occurring on the shell side of the tubes in the main body of the housing.

Alternatively the reactor can be of a similar multitube design housed in a common shell-type housing as previously described but wherein the gas and liquid are passed through the multiple tubes which function as the reactor tubes, with effluent being removed from the upper ends of the reactor tubes and heat transfer fluid is passed through the space along the outside surfaces of the reactor tubes. The reactor tubes can be either multiple individual tubes with spaces between adjacent tubes, or multiple bundles of tubes with spaces between adjacent bundles of tubes.

Likewise the entire cross section of the reactor vessel may have a plurality of shafts disposed within it, the bottoms of said shafts being located above the reaction gas inlet but extending a distance above the top surface of the reaction slurry into the gas disengaging spaces so as to create multiple single columns of standing, noncirculating liquid with catalyst suspended and dispersed in said standing liquid. The reaction zone therefore has multiple single columns, said columns having a common bottom reaction gas introduction zone and a common upper gas disengagement space. To insure proper control of the exothermic process additional tubes can be inserted into or between the multiple single columns to function as heat exchangers.

It would be an advance if, in whatever configuration the reaction vessel may take, catalyst within the reaction vessel could be more uniformly distributed and circulated so as to insure more even catalyst aging in the course of the reaction, more effective use of the catalyst by insuring a higher probability that the maximum amount of available catalyst is in the reaction zone to promote the reaction by eliminating stagnant zones of uncirculating, standing catalyst and to provide a more uniform dispersion of catalyst throughout the reaction zone.

SUMMARY OF THE INVENTION

Figure 1:
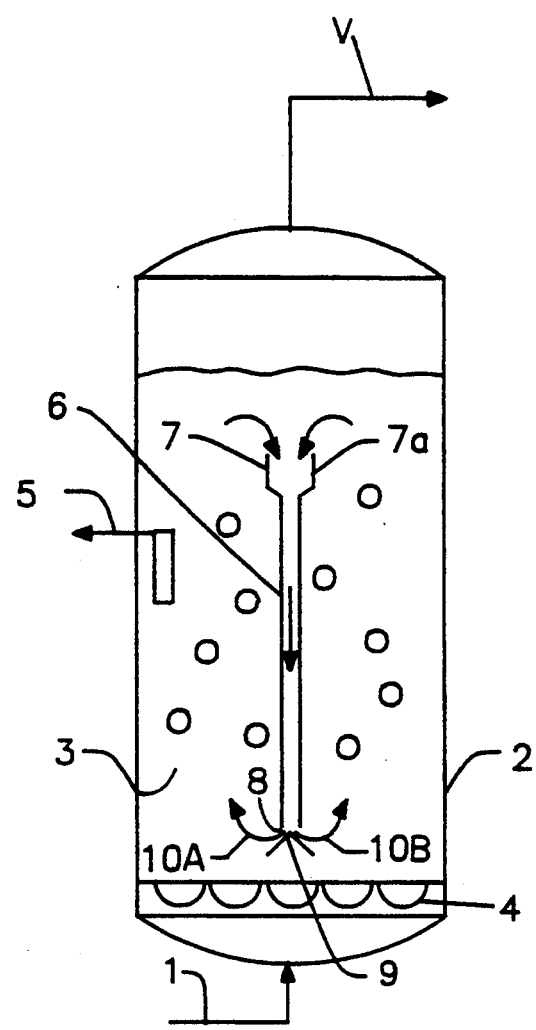
FIG. 1 is a representation of one embodiment of the catalyst circulating downcomer of the present invention employed in a slurry phase hydrocarbon synthesis process reaction vessel.

Catalyst utilization is improved in slurry phase hydrocarbon synthesis processes by circulating the catalyst in the slurry phase by means of one or more substantially vertical downcomers conduits fully immersed in the slurry phase. The substantially vertical downcomer conduits are open at both ends and extend preferably from near the bottom of the slurry phase in the hydrocarbon synthesis process reaction to just below the upper surface of the slurry phase. The top of the substantially vertical downcomer conduit is topped by gas disengagement means comprising a gas disengagement zone and a catalyst directing means. In the gas disengaging zone unreacted synthesis gases and light product gases present near the top of the slurry phase are separated from the catalyst and liquid hydrocarbon synthesis products present in the slurry phase at the same location. By disengaging the gases from the catalyst and liquid hydrocarbons, the catalyst in liquid hydrocarbon becomes a more dense mixture which consequently is free to descend into the catalyst flow directing means which is part of the gas disengagement means. The catalyst flow directing means surrounds the top rim of the downcomer conduit and passes catalyst into the top of the downcomer conduit which catalyst is then passed downward under the influence of gravity through the downcomer and is eventually discharged from the downcomer, again, solely under the influence of gravity. This catalyst flow directing means is preferably in the form of a funnel or downward pointing cone or pyramid or semi-circle etc., the angle of the walls of which is greater than the angle of repose of the solids in the slurry to facilitate the flow of catalyst from the gas disengaging zone into the downcomer. This shape directs the catalyst into the downcomer. To prevent synthesis gases from interfering with the downward circulation of catalyst in hydrocarbon slurry in the downcomer the bottom of the downcomer is shielded from gas entering by baffle means (hereinafter referred to simply as baffle or baffles) which diverts rising gases from the open bottom end of such downcomer but which baffle offers no obstacle to the downwardly moving catalyst. This baffle may take the form of an inverted channel which is at least as long and as wide as the downcomer opening. The baffle can be the form of an inverted V, cone or pyramid (point up) or a hemisphere (convex side up). Other shapes can undoubtedly be envisioned. By use of baffles of this shape rather than flat the gas is not only prevented from entry into the downcomer, but the falling catalyst stream is split and diverted away from the bottom of the downcomer at an angle which increases the probability that the falling catalyst will encounter a rising synthesis gas bubble stream, and thereby be dispersed, resulting in a more uniform distribution of catalyst over the cross-section of the reactor.

The catalyst maldistribution problem that is addressed by the use of downcomers is the axial gradient of catalyst concentration. While the energy imparted by the gas bubbles of the synthesis gas introduced into the slurry by the gas introduction means, e.g., bubble caps, spargers, multi-cone gas distributors etc., tends to disperse the catalyst in the slurry, gravity is still causing the catalyst to settle. The degree of dispersion increases with increasing gas velocity, increasing liquid velocity, increasing liquid density and decreasing particle size. For most conditions encountered in the large scale practice of hydrocarbon synthesis, there is still a large gradient of catalyst concentration from the bottom to the top of the reactor. By the use of downcomers, a high rate of liquid flow down the downcomer sets up an upward velocity in the reactor slurry outside the downcomer that helps overcome the downward pull of gravity on the catalyst particles in the slurry. This induced upward flow leads to a more uniform catalyst distribution. While the catalyst particles carried down the downcomer in the circulating slurry are a detriment to the improvement in distribution because they add to the load of the catalyst particles which must be distributed by liquid circulation, the upward flow in the overall slurry created in response to and as a consequence of the downward displacing flow in the downcomer produces a net improvement in catalyst distribution.

Because hydrocarbon synthesis productivity is dependent on good catalyst/synthesis gas interaction, the improved distribution of catalyst afforded by the present invention should result in higher productivity, better catalyst utilization, longer catalyst life, and better product selectivity.

The substantially vertical downcomer need not be placed in any specific location within the hydrocarbon synthesis reaction zone. One downcomer or multiple downcomers may be installed in each reaction zone, each downcomer being sized so as not to excessively interfere with the fluid dynamics of the reaction zone nor to occupy an excessive volume of the available volume of the reaction zone.

The substantially vertical downcomers should occupy from 0.1 to 5% in total of the available cross sectional area of the reaction zone of the slurry phase reactor, preferably 0.2 to 2% in total of the available cross sectional area of the reaction zone. When using multiple downcomers, no single downcomer should occupy more than 50% of the cross sectional area occupied by the downcomer array.

The downcomer has a nominal diameter of 1 to 12 inches, preferably 2 to 4 inches in commercially sized reactor vessels.

As previously stated the downcomer is fully immersed in the reaction slurry in the slurry phase reaction vessel. The bottom of said downcomer is near the bottom of the reaction slurry but at a height sufficiently above the bottom such that the falling catalyst exiting the bottom of the downcomer and distributed by the baffle will not accumulate on the bottom of the reaction vessel as a useless, stagnant mass of material. The bottom exit points of the distributor are ideally over the synthesis gas introduction means such as bubble caps, injection ports or multi cone gas distributor on the bottom of the reaction vessel so that the falling stream of catalyst is immediately intercepted by a rising stream of synthesis gas. Achieving the optimal targeting of the exit point can be done by tilting the downcomer around its vertical axis. In the same way the optimal location of the top catalyst entry point can be achieved. This ability to tilt the downcomer is particularly advantageous insofar as the optimal catalyst accumulation/entry point into the downcomer and catalyst exit point out of the downcomer within the reaction zone may not lie in the same vertical line but may be off axis.

The present invention is especially marked by being mechanically simple in that it requires no moving parts. It has low operating cost in that no external source of lifting gases or liquid recycles are needed. High slurry circulation is achievable when the gas is disengaged from the slurry. Gas by-passing or back mixing are also reduced.

For example, considering the entrance, exit and friction loss for the slurry flowing in a vertical pipe, a single 3-inch pipe can circulate slurry at a rate of 400 to 500 gpm. In a 4-ft diameter HCS reactor, this circulation rate can produce an upward liquid velocity of 2–3 cm/sec, which is high enough to keep most of the catalyst particles evenly distributed in the reactor.

With the slurry moving upwards along with the gas, the propensity for the gas to move downwards and for other mechanisms of gas dispersion to be operative are reduced resulting in lower gas back-mixing. The downward movement of gas free slurry (gas disengaged slurry) is through the downcomer. Even a commercial-size reactor can operate with less gas back-mixing. Once-through gas conversions will increase, less recycle gas will be needed, resulting in higher reactor productivity.

With more even catalyst distribution, reactions and heat release will no longer be concentrated in the lower section of the reactor resulting in improved reactor performance. The vertical temperature profile will be more even as the result of the higher slurry circulation, the cooling coil can be utilized more efficiently. More even catalyst distribution will also allow the unit to operate at higher inlet velocities since the bed height can be increased to achieve adequate gas residence time. This again will result in higher reactor throughput.

Improved reactor productivity will also be achieved when the downcomers of the present invention are used in combination with catalyst rejuvenation tubes disclosed and claimed in copending application, U.S. Ser. No. 07/994,215 filed even date herewith in the names of Behrmann, Pedrick and Mauldin and application, U.S. Ser. No. 07/994,219 filed even date herewith in the names of Behrmann and LeViness.

As disclosed in OP-3720B hydrocarbon synthesis catalyst which has lost activity in the HCS process can be reactivated using a rejuvenator tube which comprises a substantially vertical draft tube means, open at both ends, fully immersed in the slurry on the HCS reactor wherein rejuvenating gas such as hydrogen or a hydrogen containing gas is injected at or substantially near the bottom of said rejuvenation draft tube. The bottom of the rejuvenation draft tube is fitted with a gas deflection baffle to prevent entry of synthesis gas into said tube. The velocity of the rejuvenation gas in the tube is such that the slurry density in the tube is less than the slurry density in the overall reactor vessel. Superficial rejuvenation gas velocity in the tube is at least 0.2 to 40 times, preferably 0.5 to 20 times, more preferably 3 to 15 times the superficial gas velocities of the gases rising in the reactor vessel.

The tubes are sized so as to fit within the reaction vessel and are also sized so as to not interfere with the fluid dynamics of the vessel nor with the normal synthesis gas flow within such vessel. These tubes occupy, on a cross sectional area basis, as measured in the horizontal plane through the vertical tubes, a total of from 0.2 to 10% of the cross sectional area of the reaction vessel, preferably from 0.4 to 8%, more preferably from 0.4 to 5% of the cross sectional area basis of the reaction vessel. Ideally multiple tubes will be employed as to insure maximized catalyst rejuvenation. When multiple tubes are employed no single tube will constitute more than 50%, preferably more than 30%, more preferably more than 10% of the total cross sectional area of the draft tube array. In commercial HCS vessels such tubes will be less than 12 inches in diameter, preferably less than 8 inches and more preferably less than 6 inches in diameter.

As disclosed in application, U.S. Ser. No. 07/994,219, the degree of catalyst rejuvenation in the rejuvenation tubes can be controlled by independently controlling the rejuvenation temperatures in the rejuvenation tube as compared to the temperature of the surrounding reaction slurry. In many instances this involves conducting the rejuvenation at temperatures higher than those of the surrounding reactor. This control of the temperature in the rejuvenation tubes can be achieved either by increasing the residence time in the rejuvenation tube, so as to take advantage of the exothermic nature of the rejuvenation process itself and thereby increase the temperature, by deliberately introducing heat into the rejuvenation tube, by a combination thereof, or by introducing a cooling medium into the rejuvenation tube, thereby lowering the rejuvenation temperature.

To effectively take advantage of the heat produced by the exothermic nature of the rejuvenation process itself in the rejuvenation tubes, it is preferred that the rejuvenation tube be fitted with insulation means, thus trapping the heat in the rejuvenation tube. This insulation means can take the form of a coating of material of low heat transfer coefficient, such as ceramic. Alternatively the rejuvenation tube can be surrounded by a larger diameter tube with the annular space between the rejuvenation tube and the larger diameter tube surrounding it thus isolating it from the reaction slurry.

Alternately, heat or cooling can be introduced into the rejuvenation tube by means of a separate, independent, controllable heating or cooling means source, such as a steam heat exchanger or electrical heater, run partially or totally up the interior of the rejuvenation tube. When heating, it would be preferably to provide the maximum heat exchange near the bottom of the rejuvenation tube to provide the maximum benefit in increasing the rate and extent of rejuvenation.

When using the independent heat source/heat exchanger inside the rejuvenation tube, it is preferably to simultaneously employ an insulating wrap around the rejuvenation tube.

In this and the previous embodiment the heat exchanger extending totally up the inside the rejuvenation tube might serve the purpose of heating the contents of the rejuvenation tube in the lower region and mitigating the temperature rise (i.e. cooling) in the upper region, should reaction rates and heat of reaction be high enough to cause the temperature in the upper regions to rise to undesirable levels.

The temperature in the rejuvenation draft tube should be high enough to react out any entrained and dissolved CO in the lower part of the rejuvenation tube and react deactivating species in the wax and on the catalyst, yet low enough to avoid excessive methane production and hydrolysis of the wax. In the present invention the rejuvenation temperature in the rejuvenation tubes to achieve effective catalyst rejuvenation is controlled so as to range from about 400° to 500° F., preferably about 420° to 480° F. and more preferably about 440°–470° F. The lower temperatures are effective in those instances in which the catalyst and/or wax contain a minimum of deactivating species. Higher temperatures are needed in those instances when the catalyst and/or wax containing higher levels of deactivating species.

Hydrocarbon synthesis processes which benefit by the use of the present invention are carried out under slurry phase conditions, at elevated temperatures and pressures. Pressures typically range from 1–100 atmospheres, preferably 10–50 atmospheres, more preferably 15–40 atmospheres. Temperatures may range from about 175° C. to 450° C., preferably 175° C. to 420° C., more preferably 175° to 300° C. For Fischer-Tropsch processes hydrogen to carbon monoxide ratios in the feed gas may range from about 0.5 to 4.0, preferably 0.7 to 2.75, more preferably about 0.7 to 2.5 or other synthesis feed such as methanol, is injected at superficial gas velocities ranging from about 1 to 30 cm/sec through gas injection means such as bubble caps, spargers or multi cone arrays into the main reaction zone in which are located hydrocarbon synthesis product (i.e., hydrocarbon liquids or liquid wax) and catalyst. In slurry phase operation, the slurry usually comprises about 10 wt % to 50 wt % catalyst solids, preferably 30 wt % to 40 wt % catalysts solids. The catalyst is suspended in the slurry liquid by a combination of product recycle liquid, slurry recycle liquid, and injected synthesis gas feed. By use of the downcomer means of the present invention the distribution of the suspended catalyst in the reaction slurry is made more uniform; improved catalyst dispersion is obtained.

The slurry phase liquids in which the catalyst is dispersed are those that are liquid at reaction conditions, generally inert, and a good solvent for synthesis gas. Typically, the slurry is the product of the reaction and contains $C_{5+}$ hydrocarbons, usually $C_5$–$C_{100}$ hydrocarbons. Preferably, however, the slurry liquid comprises primarily high boiling paraffins with small amounts of primary and secondary alcohols, acids, esters, or mixtures thereof. Sulfur, nitrogen, phosphorus, arsenic, or antimony heteroatoms are to be avoided since these tend to poison the hydrocarbon synthesis catalyst. Examples of specific slurry liquids are octadecane, tetracosane, and the like. Preferred slurry materials are Fischer-Tropsch waxes and hydrocarbons larger than $C_{16}$.

The hydrocarbon synthesis reaction is highly exothermic and the heat of reaction is removed by a heat transfer material which is either circulating on the shell side of a shell and tube reactor when the reaction takes place in the tube, or through the tubes when the reaction takes place on the shell side. The common heat transfer material can be any material having a high heat capacity, whether or not it undergoes a phase change. Preferably the heat transfer fluid is boiling water.

The catalyst employed in the hydrocarbon synthesis process is any catalyst known to be active in Fischer-Tropsch synthesis. For example, Group VIII metals, whether supported or unsupported, are known Fischer-Tropsch catalysts. Of these, iron, cobalt and ruthenium are preferred, particularly iron and cobalt, most particularly cobalt.

A preferred catalyst is supported on an inorganic refractory oxide selected from Groups III, IV, V, VI, and VIII of the Periodic chart of the elements. Preferred supports include silica, alumina, silica-alumina, the Group IVB oxides, most preferably titania (primarily in the rutile form), and generally supports having a surface area of less than about 100 m²/gm, preferably 70 m²/gm and less.

The catalytic metal is present in catalytically active amounts, usually about 1–100 wt % the upper limit being attained in the case of iron catalyst, preferably 2–40 wt %, more preferably about 2–25 wt %. Promoters may be added to the catalyst and are well known in the Fischer-Tropsch catalyst art. Promoters can include ruthenium (when it is not the primary catalytic metal), rhenium, hafnium, cerium, and zirconium, and are usually present in amounts less than the primary catalytic metal (except for ruthenium which may be present in co-equal amounts), but the promoter:metal ratio should be at least about 1:10. Preferred promoters are rhenium and hafnium. Useful catalysts are described in U.S. Pat. Nos. 4,568,663; 4,663,305; 4,542,122.

Catalyst particle size is important and particle sizes may range from that which is reasonably filterable to that which is reasonably able to be dispersed in a slurry phase. Particles sizes of 1–200 microns, preferably about 20 to 150 microns meet these requirements.

Catalyst preparation may be accomplished by a variety of techniques, although catalyst preparation does not play a part in this invention and the downcomer conduit disclosed herein will improve the dispersion of the hydrocarbon synthesis catalyst however it is prepared.

A typical catalyst preparation may involve impregnation, by incipient wetness or other known techniques of, e.g., a cobalt nitrate salt onto a titania, silica, or alumina support, optionally followed or proceeded by impregnation with a promoter material, e.g., perrhenic acid. Excess liquid is removed and the catalyst precursor dried at 100° C. to 125° C. Following drying or as a continuation thereof, the catalyst is calcined at about 300° C.–500° C. to convert the salt or compound to its corresponding oxide(s). The oxide is then reduced by treatment with hydrogen or a hydrogen containing gas at about 300° C.–500° C. for a period of time sufficient to substantially reduce the oxide to the elemental or catalytic form of the metal. Some prefer an additional cycle of oxidation/reduction. Another, and sometimes preferred method for catalyst preparation is disclosed in U.S. Pat. No. 4,621,072 incorporated herein by reference.

The invention is particularly described by reference to the Figure.

In FIG. 1 the hydrocarbon synthesis gas via line (1) is fed to the reaction vessel (2) and distributed into the catalyst/hydrocarbon reaction slurry (3) by means of gas introduction means (4) such as bubble caps. The synthesis gas rises through the reaction slurry and is converted into liquid hydrocarbon product recovered via line 5. Catalyst recycle downcomer (6) is positioned in the vessel (2) and fully immersed in reaction slurry (3). Unreacted synthesis gas and light hydrocarbon product gases are disengaged from the catalyst-liquid hydrocarbon slurry in the gas disengagement zone of gas disengagement means (7–7(a)) located at the top of downcomer (6). Such gases are vented from vessel (2) through line (V). Catalyst and hydrocarbon liquid from which gas has been disengaged falls under its own weight and settles on catalyst flow directing means funnel 7(a) of the gas disengagement means and is directed by said funnel into the top of the downcomer. The catalyst and liquid hydrocarbon pass down the downcomer and exit downcomer (6) through exit orifice (8). Synthesis gases are prevented from entering the bottom of downcomer (6) through orifice (8) by baffle (9) which also serves to distribute radially the stream of descending catalyst and liquid hydrocarbon slurry exiting orifice (8) into the adjacent slurry near the bottom of vessel (2) and is picked up by rising synthesis gas exiting gas distribution means (4).

In Example 1 reference is made to different balances made at different times during a demonstration run. Table 1 presents the different balances and the conditions employed during each balance, the number of downcomers employed, the solids concentrations, reactor densities and reactor axial temperatures when the reactor slurry at different elevations within the reactor vessel for each balance.

TABLE 1

| CONDITIONS FOR DOWNCOMER EXAMPLE | | |
|---|---|---|
| | TABULATED RESULTS | |
| HCS-PDU Run-Balance | 102 | 108 |
| Downcomer Tubes in Service | 0 | 1 |
| Velocities, cm/sec | | |
| Reactor | | |
| Inlet | 15.6 | 16.0 |
| Outlet | 12.1 | 10.4 |
| Reactor Productivity, Vol CO/Hr/Vol Slurry | 74 | 98 |
| Solids Concentrations, Lb Catalyst/(Lb Catalyst + Lb Wax) | | |
| Elevation, Ft. | | |
| 0.23 | 0.4197 | 0.3191 |
| 2.52 | 0.3560 | 0.3054 |
| 5.47 | 0.3529 | 0.2660 |
| 9.41 | 0.2962 | 0.2628 |
| 13.49 | 0.2664 | 0.2791 |

TABLE 1-continued

CONDITIONS FOR DOWNCOMER EXAMPLE

| | TABULATED RESULTS | |
|---|---|---|
| 20.49 | 0.2515 | 0.2380 |
| 30.47 | 0.1321 | 0.2019 |
| Reactor Densities, Lb/Cu. Ft. | | |
| Elevation, Ft | | |
| 0.0–2.5 | 40.85 | 30.26 |
| 2.5–9.8 | 31.70 | 27.05 |
| 9.8–19.8 | 25.34 | 24.60 |
| 19.8–29.8 | 21.94 | 22.75 |
| 29.8–35.3 | 15.11 | 22.07 |
| 35.3–39.8 | 1.54 | 20.85 |
| 39.8–48.8 | 0 | 8.25 |
| Reactor Axial Temperature Profile, °F. | | |
| Elevation, Ft. | | |
| 1.0 | 404 | 425 |
| 2.0 | 406 | 426 |
| 3.0 | 408 | 426 |
| 4.0 | 410 | 427 |
| 5.0 | 411 | 428 |
| 6.0 | 411 | 428 |
| 7.0 | 411 | 428 |
| 8.0 | 412 | 428 |
| 9.0 | 412 | 428 |
| 10.0 | 412 | 428 |
| 11.0 | 412 | 430 |
| 13.0 | 412 | 428 |
| 15.0 | 412 | 429 |
| 17.0 | 410 | 428 |
| 19.0 | 410 | 429 |
| 21.0 | 410 | 429 |
| 23.0 | 408 | 429 |
| 25.0 | 408 | 429 |
| 27.0 | 408 | 430 |
| 29.0 | 407 | 429 |
| 31.0 | 407 | 430 |
| 33.0 | 407 | 432 |
| 35.0 | 404 | 430 |
| 37.0 | | 436 |
| 39.0 | | 438 |

EXAMPLE 1

The ability of a downcomer tube to improve catalyst dispersion in a reactor vessel was demonstrated in a pilot demonstration unit vessel having a 4 foot diameter and a slurry height of about 35 feet using a downcomer tube 3 inches in diameter and 32.5 feet in length. A catalyst was used which comprised 12% Co-1% Re on a support of 94% $TiO_2$-6% $Al_2O_3$, which was activated by reduction in hydrogen at about 350° C. The liquid phase of the slurry consisted of the HCS wax product which is liquid under the reaction conditions of 210°–230° C., 20 atm pressure. Feed gas composition was about 56% $H_2$-26% CO—13%$CO_2$—5% $CH_4$ (by volume). An array of cooling water tubes was present in the reactor to remove the heat of reaction.

The downcomer tube was provided at its upper end with a flared inlet having a 2 sq. ft cross sectional area that allowed gas to be disengaged from the incoming liquid, which served to maximize the density difference between the down-flowing fluid in the downcomer and the fluid surrounding the downcomer. It is this density difference that provides the driving force for the liquid flow in the downcomer. The downcomer is "turned on" by increasing the level of the slurry in the reactor to above the level of the inlet at the top of the downcomer tube and reducing to a negligibly low value any purge gas to the downcomer tube. During its period of operation the catalyst distribution through the reactor, as evidenced by catalyst density measurements taken at different heights in the vessel, markedly improved.

Figure 2:
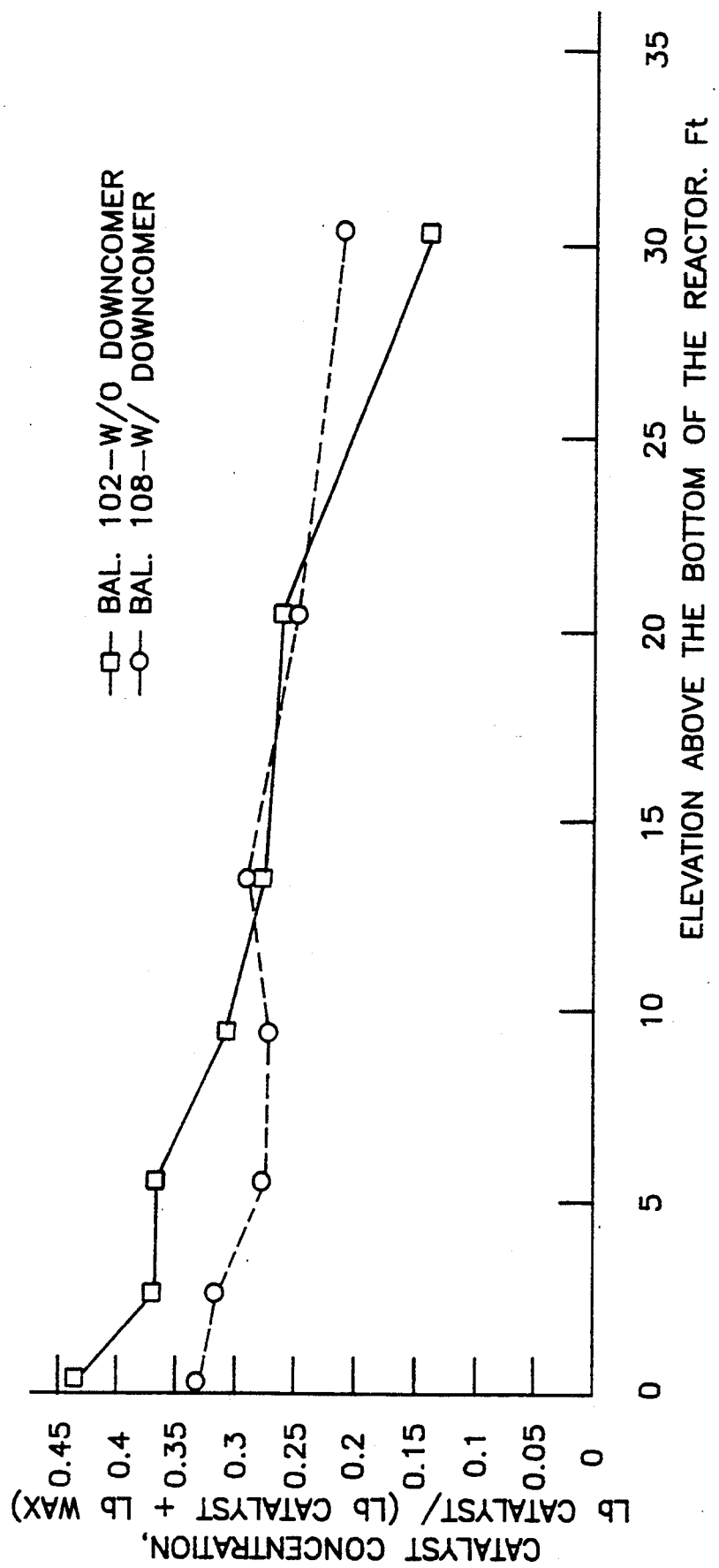
FIG. 2 presents the operation of a single downcomer tube and shows it flattens the catalyst concentration profile as compared to the profile when no tube is in use.
Figure 3:
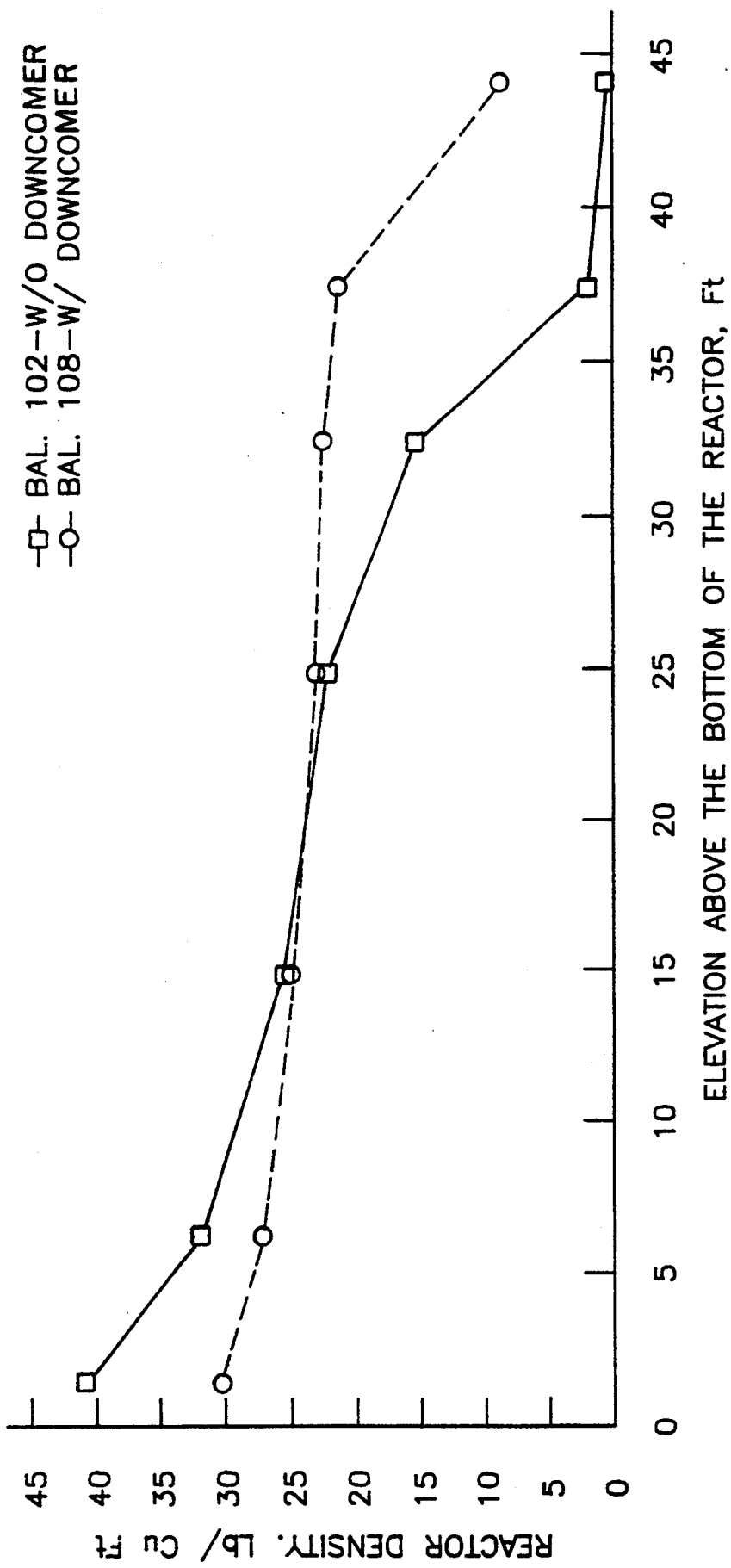
FIG. 3 presents the operation of a single downcomer tube and shows that it flattens the axial catalyst density profile in the reactor as compared to the profile when no tube is in use.
Figure 4:
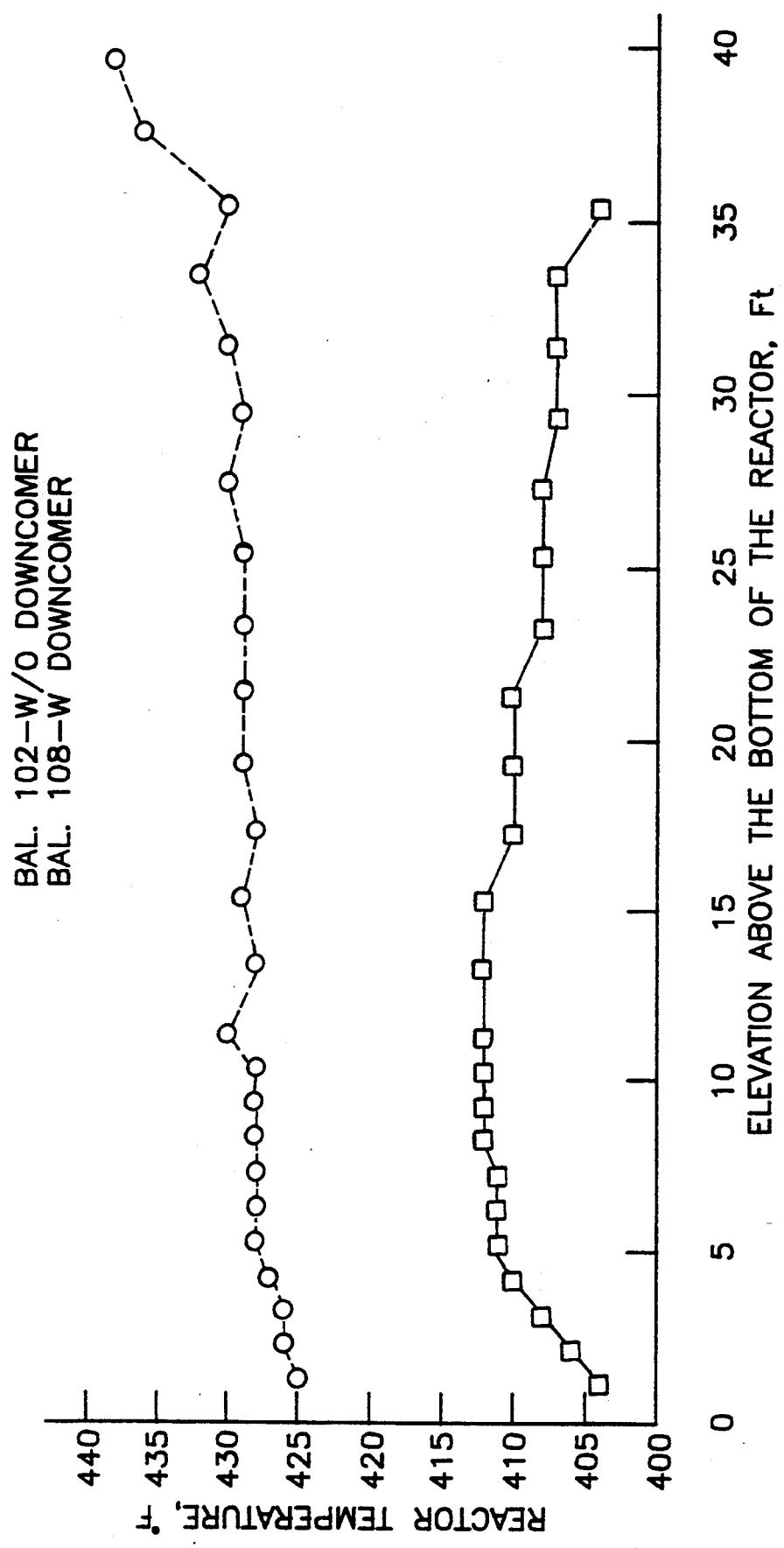
FIG. 4 presents the operation of a single downcomer tube and shows that it flattens the temperature profile within the slurry in the reactor.

FIGS. 2 and 3 compare the catalyst concentration and axial catalyst density profiles for a balance in which the downcomer was operative (Balance 108) with one in which no catalyst dispersion downcomer device was used (Balance 58). The single downcomer tube gave significantly flattened catalyst concentration and axial catalyst density profiles across the depth of the slurry on the reactor. FIG. 4 compares the axial temperature profiles in the reactor for Balances 108 and 102. This figure shows that this single downcomer was extremely effective in shifting the temperature profile in the slurry in the reactor, as would be expected from the more uniform catalyst distribution produced and the displacement of catalyst from the bottom of the reaction zone by the downwardly moving material exiting the bottom of the downcomer.

In Example 2 reference is made to balances 58 and 85 at different times during a demonstration run. Table 2 presents the different balances and the conditions employed during each balance, the number of downcomers employed, the number of rejuvenation tubes employed, gas velocities in the tubes, the solids concentrations, reactor densities and reactor axial temperatures when the reactor slurry at different elevations within the reactor vessel for each balance. In both reported balances reference is made to "rejuvenation tubes". These tubes are open ended vertical tubes extending from the bottom of the slurry to just below the top surface of the slurry. Rejuvenation gas, in this case hydrogen, is injected into the bottom of such tube to rejuvenate the catalyst drawn into the bottom of said tube and ejected out of the top, thereby circulating reactivated catalyst. The use of rejuvenation tubes for catalyst reactivation and circulation is the subject matter of copending application, U.S. Ser. No. 07/994,215 filed even date herewith in the names of Pedrick, Mauldin and Behrmann.

TABLE 2

CONDITIONS FOR DOWNCOMER EXAMPLE

| | TABULATED RESULTS | |
|---|---|---|
| HCS-PDU Run-Balance | 58 | 85 |
| Downcomer Tubes in Service | 0 | 1–3" φ |
| Rejuvenation Tubes in Service | 1–3" φ | 2–3" φ |
| Velocities, cm/sec | | |
| Reactor | | |
| Inlet | 14.6 | 14.6 |
| Outlet | 12.1 | 12.1 |
| Lift Tube | 7.3 | N.A. |
| Rejuvenation Tubes | 74.8 | 38.2 |
| Reactor Productivity, Vol CO/Hr/ Vol Slurry | 61 | 59 |
| Solids Concentrations, Lb Catalyst/(Lb Catalyst + Lb Wax) | | |
| Elevation, Ft. | | |
| 0.23 | 0.4518 | 0.3450 |
| 2.52 | 0.3627 | 0.2126 |
| 5.47 | 0.3189 | 0.2367 |
| 9.41 | 0.2380 | 0.2246 |
| 13.49 | 0.1994 | 0.2230 |
| 20.49 | 0.1127 | 0.2132 |
| 30.47 | 0.0969 | 0.1648 |
| Reactor Densities, Lb/Cu. Ft. | | |
| Elevation, Ft. | | |
| 0.0–2.5 | 37.65 | 27.75 |
| 2.5–9.8 | 28.74 | 25.65 |
| 9.8–19.8 | 20.82 | 22.88 |
| 19.8–29.8 | 17.91 | 21.68 |
| 29.8–35.3 | 16.87 | 22.68 |
| 35.3–39.8 | 1.12 | 18.05 |

TABLE 2-continued

CONDITIONS FOR DOWNCOMER EXAMPLE

|  | TABULATED RESULTS | |
| --- | --- | --- |
| 39.8–48.8 | 0 | 1.72 |
| Reactor Axial Temperature Profile, °F. | | |
| Elevation, Ft. | | |
| 1.0 | 424 | 420 |
| 2.0 | 425 | 421 |
| 3.0 | 427 | 422 |
| 4.0 | 428 | 423 |
| 5.0 | 429 | 424 |
| 6.0 | 427 | 424 |
| 7.0 | 427 | 424 |
| 8.0 | 427 | 424 |
| 9.0 | 426 | 424 |
| 10.0 | 425 | 424 |
| 11.0 | 426 | 426 |
| 13.0 | 423 | 424 |
| 15.0 | 423 | 425 |
| 17.0 | 421 | 424 |
| 19.0 | 421 | 425 |
| 21.0 | 421 | 425 |
| 23.0 | 419 | 424 |
| 25.0 | 419 | 425 |
| 27.0 | 418 | 425 |
| 29.0 | 417 | 425 |
| 31.0 | 417 | 426 |
| 33.0 | 417 | 426 |
| 35.0 | 414 | 423 |
| 37.0 |  | 428 |
| 39.0 |  | 428 |

EXAMPLE 2

The ability of a downcomer tube to improve catalyst dispersion in a reactor vessel was demonstrated in the pilot demonstration unit described in Example 1.

Catalyst concentration and axial catalyst density profiles for a balance in which the downcomer was operative (Balance 85) with one in which no catalyst dispersion downcomer device was used (Balance 58) are compared in Table 2. The single downcomer tube gave significantly flattened catalyst concentration and axial catalyst density profiles across the depth of the slurry on the reactor. The Table also shows that this single downcomer was extremely effective in shifting the temperature profile in the slurry in the reactor, as would be expected from the more uniform catalyst distribution produced and the displacement of catalyst from the bottom of the reaction zone by the downwardly moving material exiting the bottom of the downcomer.

In Balance 58 which employed no downcomer one 3" rejuvenator tube was used to rejuvenate and circulate catalyst in the slurry. A superficial gas velocity of 74.8 cm/sec was employed with that single tube. In Balance 85, which employed a downcomer, two 3" rejuvenator tubes were also used for catalyst regeneration and circulation but the superficial gas velocity in those two rejuvenator tubes was only 38.2 cm/sec meaning that the total gas flow in those two tubes merely equalled the gas flow on the single tube used in Balance 58, the improvement in catalyst distribution and temperature profile, therefore, being attributable to the use of the downcomer.

What is claimed is:

1. A method for uniformly redistributing particulate catalyst in a slurry phase reactor, said method comprising using a substantially vertical conduit means open at both ends, fully submerged in the slurry of the slurry phase reactor, the bottom end of the substantially vertical conduit means is near the bottom of the slurry phase reactor and the top of the conduit means is topped by gas disengaging means which are below the top surface of the slurry in the slurry phase reactor and wherein the bottom of the substantially vertical conduit means is shielded by a baffle means which diverts gases rising from the bottom of the slurry phase reactor from entering into the bottom of the substantially vertical conduit whereby catalyst in slurry enters at the top of the substantially vertical conduit and is disengaged from gases present therein thereby becoming a more dense mixture of catalyst in slurry which passes down the substantially vertical conduit and is ejected from the bottom of said conduit near the bottom of the slurry phase reactor.

2. The method of claim 1 wherein the baffle at the bottom of the substantially vertical conduit means is in the form of an inverted cone whereby downwardly moving catalyst-liquid stream exiting the bottom of the substantially vertical conduit impinges on the inverted cone and is diverted away from the bottom of the substantially vertical conduit at an angle.

3. The method of claim 1 wherein the substantially vertical conduit means comprises one or more downcomers.

4. The method of claim 3 wherein the cross sectional surface area of the substantially vertical conduit means occupies from 0.1 to 5% of the available cross sectional surface area of the reaction zone of the slurry phase reactor.

5. The method of claim 4 wherein when a multiple downcomer array is employed no single downcomer within the array constitutes more than 50% of the total cross sectional area of the multiple downcomer array.

6. A method for simultaneously uniformly redistributing and rejuvenating particulate catalyst in a slurry phase reactor, said method (1) comprising using a substantially vertical conduit means open at both ends, fully submerged in the slurry in the slurry phase reactor, the bottom end of the substantially vertical conduit means is near the bottom of the slurry phase reactor and the top of the conduit means is topped by gas disengaging means which are below the top surface of the slurry in the slurry phase reactor whereby catalyst in slurry enters at the top of the substantially vertical conduit means and is disengaged from gases present therein thereby becoming a more dense mixture of catalyst in slurry which passes down the substantially vertical conduit and is ejected from the bottom of said conduit near the bottom of the slurry phase reactor, thereby redistributing the catalyst, and (2) comprising using a substantially vertical draft tube means open at both ends, fully immersed in the slurry containing the catalyst and injecting hydrogen containing gas at or substantially near the bottom of said draft tube means thereby lifting catalyst in slurry from the bottom of the slurry phase reactor into and through the open bottom end of the draft tube means, rejuvenating catalyst in the presence of said hydrogen containing gas in the vertical draft tube means and ejecting the rejuvenated catalyst into the top of the slurry phase in the slurry phase reactor through the open top of the draft tube means.

* * * * *